US00PP21428P2

(12) United States Plant Patent
Bernabe

(10) Patent No.: US PP21,428 P2
(45) Date of Patent: Oct. 26, 2010

(54) ***SALVIA* PLANT NAMED 'MELEN'**

(50) Latin Name: *Salvia jamensis*
Varietal Denomination: Melen

(76) Inventor: Catherine Bernabe, Saint Gueltas, Henansal (FR) 22400

( * ) Notice: Subject to any disclaimer, the term of this patent is extended or adjusted under 35 U.S.C. 154(b) by 0 days.

(21) Appl. No.: 12/459,824

(22) Filed: Jul. 7, 2009

(51) Int. Cl.
*A01H 5/00* (2006.01)

(52) U.S. Cl. ..... Plt./475

(58) Field of Classification Search ..... Plt./475
See application file for complete search history.

(56) References Cited

OTHER PUBLICATIONS

UPOV-ROM PBR 20080766, published Jun. 15, 2008.*

* cited by examiner

*Primary Examiner*—Annette H Para
*Assistant Examiner*—Louanne C Krawczewicz Myers

(57) ABSTRACT

A new and distinct *Salvia* cultivar named 'MELEN' is disclosed, characterized by distinctive yellow calyx and dark brown corolla, large individual flower size and early flowering. 'MELEN' is highly floriferous and has an upright plant habit. The new variety is a *Salvia,* normally produced as an outdoor garden or container plant.

1 Drawing Sheet

Figure 1:
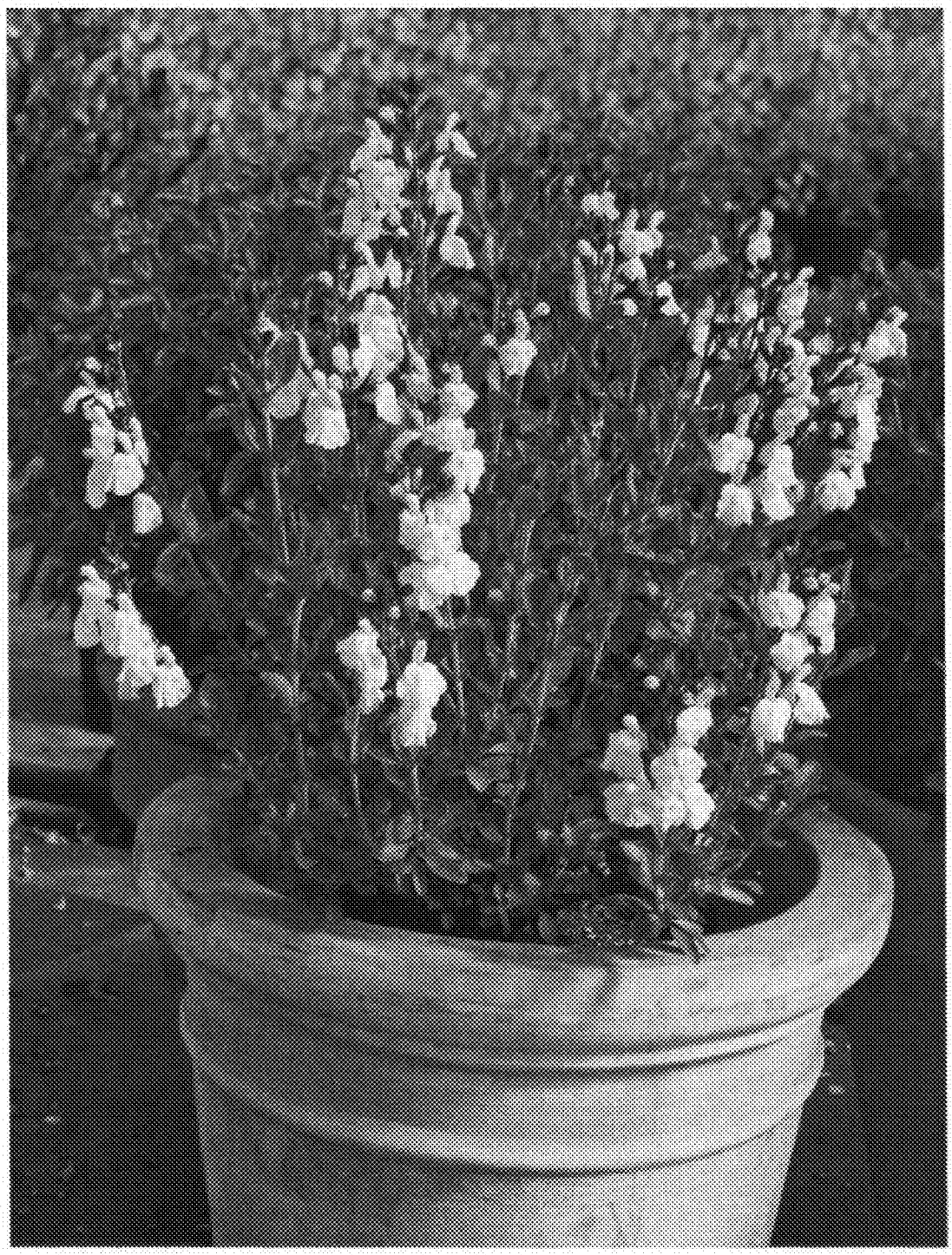

Latin name of the genus and species: *Salvia jamensis.*
Variety denomination: 'MELEN'.

BACKGROUND OF THE INVENTION

The new cultivar is a product of a planned breeding program conducted by the inventor, Catherine Bernabe, a citizen of France. The objective of the breeding program was to produce highly floriferous plants of *Salvia jamensis* in a variety of colors. Plants of the unpatented variety *Salvia jamensis* were self-crossed during the Summer of 2001, at a commercial nursery in Henansal, France. The new variety was discovered in the Summer of 2003, at the same commercial nursery by the inventor, Catherine Bernabe, in a group of seedlings resulting from that crossing.

Asexual reproduction of the new cultivar 'MELEN' by vegetative cuttings was performed at the same commercial greenhouse in Henansal, France in 2005 and has shown that the unique features of this cultivar are stable and reproduced true to type on successive generations. All plants of 'MELEN' have been kept confidentially at the nursery in Henansal, France, with the exception of those supplied for Plant Breeders' Rights testing in Spring of 2009. Plant Breeders' Rights were applied for in April of 2008, however, there has been no commercial distribution or access to the variety.

SUMMARY OF THE INVENTION

The cultivar 'MELEN' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'MELEN' These characteristics in combination distinguish 'MELEN' as a new and distinct *Salvia* cultivar:

1. Distinctive yellow calyx and dark brown corolla.
2. Large individual flower size.

3. Compact and upright plant habit.
4. Early flowering.
5. Highly floriferous.

Plants of the new cultivar 'MELEN' are similar to plants of the parent, *Salvia jamensis* unpatented, in most horticultural characteristics, however, plants of the new cultivar 'MELEN' produces larger flowers than the parent variety, with longer inflorescence.

COMMERCIAL COMPARISON

Plants of the new cultivar 'MELEN' can also be compared to *Salvia microphylla*. Plants of 'MELEN' are similar to plants of, *Salvia microphylla*, unpatented, in most horticultural characteristics, however, plants of the new cultivar 'MELEN' produces larger flowers, with longer inflorescence. 'MELEN' also flowers earlier than *Salvia microphylla*, and produces overall more flowers and more inflorescence than *Salvia microphylla.*

Plants of the new cultivar 'MELEN' can also be compared *Salvia greggii* 'Yellow', unpatented. Plants of 'MELEN' are similar to plants of, *Salvia greggii* 'Yellow' in most horticultural characteristics, however, plants of the new cultivar 'MELEN' produce a dark corolla, compared to the green corolla of *Salvia greggii* 'Yellow'. 'MELEN' also produces darker yellow flowers.

BRIEF DESCRIPTION OF THE PHOTOGRAPH

The accompanying photograph in FIG. 1 illustrates in full color a typical plant of 'MELEN' in an approximately 2 liter pot. Age of the plant photographed is approximately 30 weeks from a rooted cutting. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'MELEN' plants grown in an unheated plastic covered greenhouse at a commercial nursery in Henansal, France. The growing temperature ranged from 8° C. to 28° C., day and night. The nursery area is un-shaded, giving bright, normal sunlight conditions. Measurements and numerical values represent averages of typical plant types.

Botanical classification: *Salvia jamensis* 'MELEN'

PROPAGATION

Time to initiate roots: About 10 days at approximately 20° C.

Time to produce a rooted cutting: About 20 to 25 days at 20° C.

PLANT

Plant spread: Approximately 35 to 40 cm.

Growth rate: Moderate, approximately 40 cm during a growing season, reaching a mature height near 60 cm after one year.

Length of primary lateral branches: Approximately 25 cm from stem to just under the inflorescence.

Diameter of lateral branches: Approximately 0.3 cm.

Quantity of lateral branches: About 35 to 40.

Stem:

- *Color.*—Youngest: Near RHS Yellow Green 145A. Oldest: Near RHS Greyed-Purple 187A.
- *Texture/pubescence.*—Smooth, non-pubescent.

Internode length: Approximately 3 to 4 cm.

Age of plant described: Approximately 30 weeks from a rooted cutting in early spring

FOLIAGE

Leaf:

- *Arrangement.*—Opposite.
- *Quantity.*—Approximately 16 per lateral branch.
- *Average Length.*—Approximately 3 cm.
- *Average width.*—Approximately 1.2 cm.
- *Shape of blade.*—Elliptic to oblong.
- *Apex.*—Obtuse.
- *Base.*—Attenutate.
- *Attachment.*—Stalked.
- *Margin.*—Crenate.
- *Texture of top surface.*—Glossy.
- *Pubescence.*—Slightly on top face, none on under surface.
- *Color.*—Young foliage upper side: Near RHS Yellow green 144A. Young foliage under side: Near RHS Yellow green 146B. Mature foliage upper side: Near RHS yellow green 144A. Mature foliage under side: Near RHS yellow green 144A.
- *Venation.*—Type: Pinnate. Venation color upper side: Near RHS yellow green 145B. Venation color under side: Near RHS yellow green 144D.
- *Petiole.*—Average Length: Approximately 0.8 cm. Diameter: Approximately 0.1 cm. Color: Near RHS yellow green 145B.

FLOWER

Natural flowering season: May to November.

Inflorescence type and habit: Bilabiate flowers arranged in verticillasters on spikes.

Flower longevity on plant: Approximately 8 days.

Quantity of flowers: About 8 to 10 buds and 6 to 8 fully opened flowers per lateral branch, at one time; or about 50 to 60 blooming spikes per plant.

Inflorescence size:

- *Diameter/width.*—Approximately 6 cm.
- *Height.*—Approximately 13 to 16 cm.

Peduncle:

- *Length.*—0.5 cm.
- *Diameter.*—0.1 cm.
- *Color.*—Near RHS Greyed-Purple N187A.
- *Orientation.*—Straight, with an outward curve towards the apex, at approximately a 30 degrees angle.
- *Strength.*—Rigid.

Petals

- *Petal arrangement.*—Bilabiate flower, with lip 2 fused petals, upper lip 3 tightly fused petals.
- *Margin.*—Entire.
- *Tip shape.*—Obtuse, with some ruffling on lower lip.
- *Length.*—Lower lip: Approximately 3.5 cm upper lip: Approximately 3.0 cm.
- *Width.*—Lower lip: Approximately 2.0 cm upper lip: Approximately 0.5 cm.
- *Petal quantity.*—5, with 2 fused on lower lip, 3 fused on upper lip.
- *Petal apex shape.*—All obtuse.
- *Texture.*—Matte.
- *Aspect.*—Mainly flat.

Color:

- *Petals.*—When opening: Upper surface: Near RHS Yellow-Orange 19A and 19B mixed with Orange-Red N30A. Lower surface: Near RHS Yellow-Orange 19A and 19B mixed with Orange-Red N30A.
- *Fully opened.*—Upper surface: Near RHS Yellow 12C with Yellow 4B. Lower surface: Near RHS Yellow 12C with Yellow-Orange 19B and 19C.

Bud:

- *Shape.*—Elongated cylinder.
- *Length.*—1.5 cm.
- *Diameter.*—0.4 cm.
- *Color.*—Near RHS Greyed-Purple N187.

Sepals:

- *Shape.*—Quantity per flower: 3.
- *Length.*—Approximately 1.4 cm.
- *Width.*—Approximately Approximately 0.6 cm fused on base.
- *Margin.*—Entire.
- *Texture.*—Slightly pubescent.
- *Color.*—Near RHS Greyed-Purple 187A.

REPRODUCTIVE ORGANS

Stamens:

- *Number.*—2.
- *Filament length.*—Approximately 1.5 cm.

Anthers:

- *Shape.*—Linear.
- *Length.*—Approximately 0.2 cm.
- *Color.*—Near RHS Grey-Brown 199B.
- *Pollen.*—Color: Near RHS Yellow-Orange 14B. Quantity: Scant.

Pistil:

- *Number.*—1.
- *Length.*—Approximately 3.1 cm.

*Style.*—Length: Approximately 2.8 cm. Color: Near RHS Red 36D.

*Stigma.*—Color: Near RHS Red 36D with light flushing near Red-Purple N74B. Ovary color: Near RHS Yellow 9C.

OTHER CHARACTERISTICS

Seeds and fruits: 4 spherical seeds per flower, each less than 0.1 cm in diameter.

Disease/pest resistance: Neither resistance nor susceptibility to pathogens and pests common to *Salvia* have been observed.

Temperature tolerance: The new variety tolerates temperatures between 5 to 35° C.

What is claimed is:

1. A new and distinct cultivar of *Salvia* plant named 'MELEN' as herein illustrated and described.

* * * * *